US011865285B2

(12) United States Patent
Papanastassiou

(10) Patent No.: US 11,865,285 B2
(45) Date of Patent: Jan. 9, 2024

(54) SYSTEMS AND METHODS FOR EVACUATING SUBDURAL HEMATOMAS

(71) Applicant: The Board of Regents, The University of Texas System, Austin, TX (US)

(72) Inventor: Alexander Papanastassiou, San Antonio, TX (US)

(73) Assignee: The Board of Regents, The University of Texas System, Austin, TX (US)

( * ) Notice: Subject to any disclaimer, the term of this patent is extended or adjusted under 35 U.S.C. 154(b) by 492 days.

(21) Appl. No.: 16/954,106

(22) PCT Filed: Dec. 14, 2018

(86) PCT No.: PCT/US2018/065818
§ 371 (c)(1),
(2) Date: Jun. 15, 2020

(87) PCT Pub. No.: WO2019/118910
PCT Pub. Date: Jun. 20, 2019

(65) Prior Publication Data
US 2020/0353134 A1 Nov. 12, 2020

Related U.S. Application Data

(60) Provisional application No. 62/599,644, filed on Dec. 15, 2017.

(51) Int. Cl.
*A61M 27/00* (2006.01)
*A61M 1/00* (2006.01)

(52) U.S. Cl.
CPC ............ *A61M 27/006* (2013.01); *A61M 1/73* (2021.05); *A61M 1/77* (2021.05); *A61M 1/85* (2021.05);
(Continued)

(58) Field of Classification Search
CPC ........ A61M 1/77; A61M 27/006; A61M 1/73; A61M 1/85; A61M 2027/004;
(Continued)

(56) References Cited

U.S. PATENT DOCUMENTS 5,029,584 A * 7/1991 Smith ................ A61B 5/02042
600/371
8,292,856 B2 * 10/2012 Bertrand ................ A61M 1/74
604/9
(Continued)

FOREIGN PATENT DOCUMENTS

| EP | 1382291 A2 | 1/2004 |
|---|---|---|
| EP | 1749549 A1 | 2/2007 |
| WO | 97/48425 A2 | 12/1997 |

OTHER PUBLICATIONS

European Extended Search Report, EP App. No. 18889473.7, dated Sep. 23, 2021 (7 pages).
(Continued)

*Primary Examiner* — Andrew J Mensh
(74) *Attorney, Agent, or Firm* — Thomas | Horstemeyer, LLP

(57) ABSTRACT

In one embodiment, a system for evacuating subdural hematomas includes an inlet configured to be placed in fluid communication with a subdural space, an irrigation reservoir in fluid communication with the inlet and configured to supply irrigation fluid to the inlet and the subdural space, an outlet separate from the inlet and also configured to be placed in fluid communication with the subdural space, and a pump in fluid communication with the outlet and configured to create negative pressure within the subdural space and evacuate fluid from the subdural space.

28 Claims, 2 Drawing Sheets

(52) U.S. Cl.
CPC ............... *A61M 2027/004* (2013.01); *A61M 2205/3306* (2013.01); *A61M 2205/3331* (2013.01); *A61M 2205/502* (2013.01); *A61M 2205/52* (2013.01); *A61M 2210/0693* (2013.01)

(58) Field of Classification Search
CPC .. A61M 2205/3306; A61M 2205/3331; A61M 2205/502; A61M 2205/52; A61M 2210/0693; A61B 2217/005; A61B 2217/007
USPC .......................................................... 604/28
See application file for complete search history.

(56) References Cited

U.S. PATENT DOCUMENTS

| | | | |
|---|---|---|---|
| 2005/0043673 A1* | 2/2005 | Lieberman | A61M 3/0283 604/28 |
| 2008/0033400 A1 | 2/2008 | Holper et al. | |
| 2008/0097276 A1 | 4/2008 | Bertrand et al. | |
| 2011/0178455 A1* | 7/2011 | Burnett | A61M 27/006 604/9 |
| 2011/0282263 A1* | 11/2011 | Branch, Jr. | A61M 25/01 604/8 |
| 2012/0053506 A1* | 3/2012 | Ludvig | A61M 27/002 604/9 |
| 2012/0172791 A1 | 7/2012 | Odland | |
| 2014/0364821 A1* | 12/2014 | Gibbons | A61M 27/00 604/319 |
| 2015/0094644 A1 | 4/2015 | Lenihan et al. | |
| 2017/0027604 A1* | 2/2017 | Wallace | A61B 17/22 |

OTHER PUBLICATIONS

Office action dated Dec. 15, 2022 in co-pending Chinese patent application No. 2018800866852 filedJul. 16, 2020.
Notice of Preliminary Rejection dated May 9, 2023 in co-pending Korean Patent Application No. 10-2020-7019491.
Notice of Deficiencies dated Jun. 8, 2023 in co-pending Israeli Patent Application No. 275403.

* cited by examiner

SYSTEMS AND METHODS FOR EVACUATING SUBDURAL HEMATOMAS

CROSS-REFERENCE TO RELATED APPLICATIONS

This application is the 35 U.S.C. § 371 national stage application of PCT Application No. PCT/US18/65818, filed Dec. 14, 2018, where the PCT claims the benefit of and priority to U.S. Provisional Application Ser. No. 62/599,644, filed Dec. 15, 2017, both of which are herein incorporated by reference in their entireties.

BACKGROUND

Subdural hematomas are a type of hematoma often associated with traumatic brain injury in which blood gathers between the dura mater and the brain. Subdural hematomas may cause an increase in intracranial pressure (ICP), which can cause compression of and damage to the delicate brain tissue. Accordingly, subdural hematomas are often life-threatening when acute.

Currently, acute subdural hematomas are typically treated by forming one or more relatively large burr holes in the cranium to the subdural space to enable collected fluid and other materials to drain from the space. More recently, minimally-invasive techniques have been developed in which small intracranial bolts are threaded into the cranium to the subdural space to enable drainage.

While such techniques can be effective, they often are not and recurrence of a subdural hematoma is relatively common. In view of this, it can be appreciated that it would be desirable to have alternative systems and methods for evacuating subdural hematomas.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have alternative systems and methods for evacuating subdural hematomas. Disclosed herein are examples of such systems and methods. In some embodiments, a system for evacuating subdural hematomas comprises an inlet through which an irrigation liquid, such as saline, can be delivered to the subdural space and a separate outlet through which liquid and other materials, such as clot material and/or other byproducts of the subdural hematoma, can be evacuated. In some embodiments, the inlet and outlet each comprise a relatively small diameter intracranial bolt having an internal passage through which fluid and other materials can pass. The inlet is in fluid communication with an irrigation reservoir that contains the irrigation fluid and the outlet is in fluid communication with a pump that creates negative pressure within the subdural space to draw out liquid and other materials from the space. In some instances, the negative pressure may also help re-expand the brain back into the subdural space that was previously occupied by the hematoma. Operation of the pump can be controlled with a pump controller that receives pressure signals from pressure sensors associated with the inlet and the outlet so that the desired level of negative pressure can be maintained and the pump can be shut off if an unintended consequence occurs, such as a clog or leak in the system 10. In some embodiments, the system further includes one or more monitoring sensors that can be used to identify one or more parameters of the evacuated fluid, such as its composition. The acquired data can be analyzed using one or more appropriate algorithms that are executed on an associated computer system.

In the following disclosure, various specific embodiments are described. It is to be understood that those embodiments are example implementations of the disclosed inventions and that alternative embodiments are possible. All such embodiments are intended to fall within the scope of this disclosure.

Figure 1:
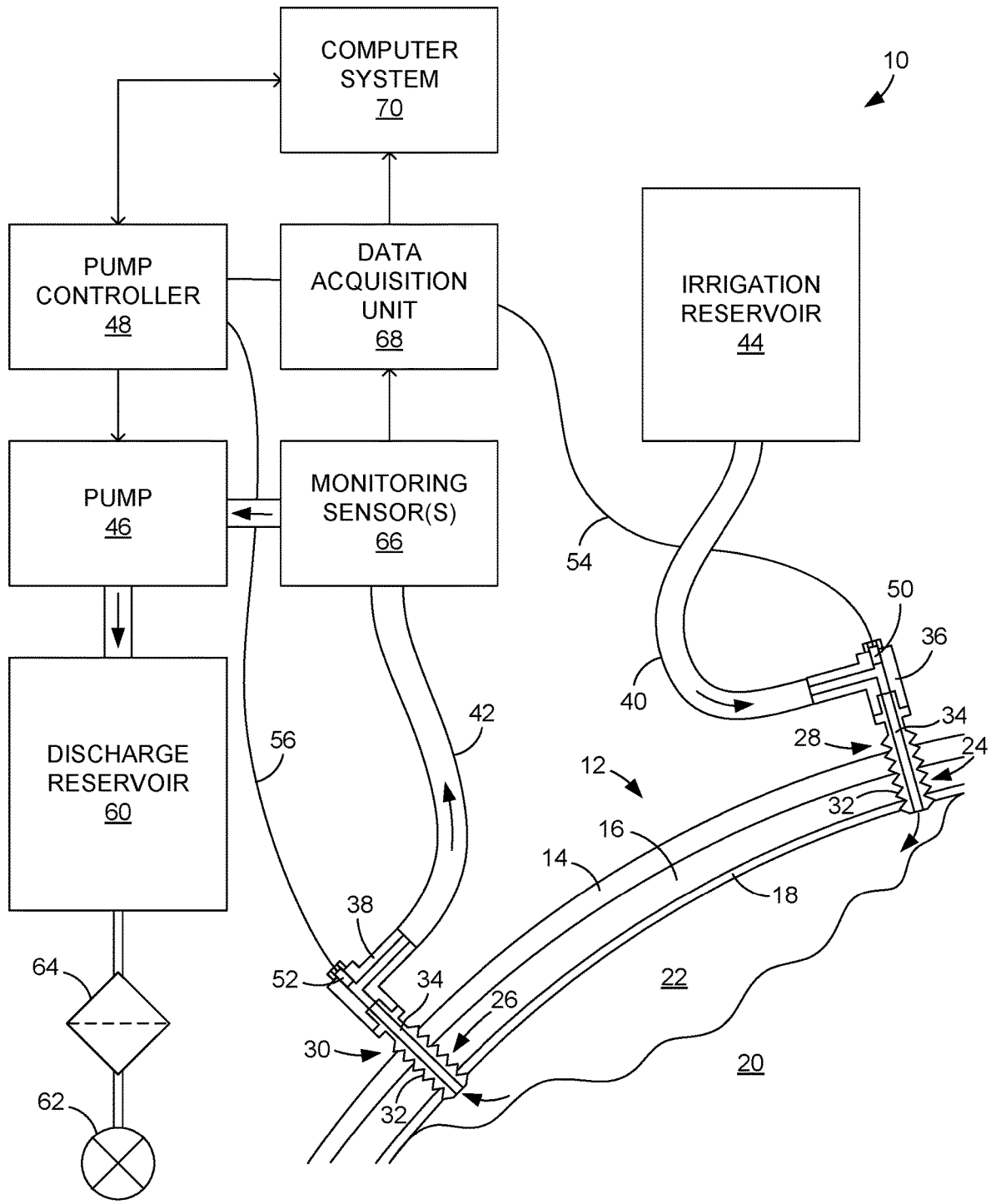
FIG. 1 is a block diagram of an embodiment of a system for evacuating subdural hematomas.

FIG. 1 illustrates an example embodiment of a system for evacuating subdural hematomas. In FIG. 1, a patient 12 is shown. More particularly, a portion of a patient's head 12 is shown while the patient is lying supine. Visible in this partial view is the patient's scalp 14 that overlies the patient's cranium 16, as well as the dura mater 18, which is shown in contact with the cranium. Between the dura mater 18 and the brain 20 is a subdural space 22 that is assumed to contain a subdural hematoma. As such, reference numeral 22 can be said to identify both the subdural space as well as the subdural hematoma.

As is further illustrated in FIG. 1, two spaced openings have been formed through the head 12 to provide access to the subdural space 22. These openings include an inlet opening 24 that can, for example, be located at the inferior position of the head and an outlet opening 26 that can, for example, be located at the superior position of the head. In such an arrangement, the outlet opening 26 can be higher than the inlet opening 24 so as to facilitate the removal of gas (e.g., air) from the subdural space 22. In some embodiments, the openings 24, 26 can be spaced apart from each other by a distance of approximately 2 to 4 inches along the head 12. The openings 24, 26 can be formed in any suitable manner. By way of example, the openings 24, 26 can be formed by making a stab incision through the scalp 14 and drilling through the cranium 16 and dura mater 18 using a twist drill. The dura may be opened sharply or bluntly through the twist drill hole if it not opened with the drill.

Once the openings 24, 26 have been formed, intracranial bolts can be provided in the openings. More specifically, an inlet intracranial bolt 28 can be threaded into the inlet opening 24 and an outlet intracranial bolt 30 can be threaded into the outlet opening 26. As can be appreciated from FIG. 1, each bolt 28, 30 includes external threads 32 that can bite into the bone of the cranium 16. In addition, each bolt 28, 30 includes an internal passage 34 through which fluid and other material can pass. With these passages 34, each bolt 28, 30 is placed in fluid communication with the subdural space 22. While intracranial bolts are illustrated in FIG. 1 and described herein, it is noted that in alternative embodiments, traditional burr holes can be formed and burr-hole covers used to secure subdural catheters in place.

With further reference to FIG. 1, an inlet manifold 36 is connected to the inlet intracranial bolt 28 and an outlet manifold 38 is connected to the outlet intracranial bolt 30. These manifolds 36, 38 enable the bolts 28, 30 to be respectively connected to an inlet tube 40 and outlet tube 42. The inlet tube 40 is also connected to an irrigation reservoir 44 and, therefore, places the irrigation reservoir in fluid communication with the inlet manifold 36 and the inlet intracranial bolt 28. As such, irrigation fluid, such as saline, contained in the irrigation reservoir 44 can flow under the force of gravity or a pump (not shown) to the inlet intracranial bolt 28 and into the subdural space 22. It is noted that the inlet intracranial bolt 28 and the inlet manifold 36 may together be referred to as the "inlet" of the system 10, while the outlet intracranial bolt 30 and the outlet manifold 38 may together be referred to as the "outlet" of the system.

The outlet tube 42 is also connected to a pump 46, such as a peristaltic pump, so that the outlet manifold 38 and outlet intracranial bolt 30 are placed in fluid communication with the pump. The pump 46 operates to draw fluid from the subdural space 22 via the outlet intracranial bolt 30 and the outlet manifold 38, as well as to create a negative pressure condition within the space. In some embodiments, operation of the pump 46 is controlled by a pump controller 48 that receives feedback from pressure sensors of the system 10. In some embodiments, the pressure sensors include an inlet pressure sensor 50 associated with the inlet and an outlet pressure sensor 52 associated with the outlet. In the example of FIG. 1, the inlet pressure sensor 50 is provided within the inlet manifold 36 and the outlet pressure sensor 52 is provided within the outlet manifold 38. Regardless of their positions, the inlet and outlet pressure sensors 50, 52 provide pressure signals to the pump controller 48 via signal lines 54 and 56 and the pump controller can modulate the pump 46 responsive to those signals to ensure that a desired negative pressure is maintained within the subdural space 22. In some embodiments, the pressure within the subdural space 22 is maintained at approximately −1 to −8 mmHg during the procedure. As mentioned above, this negative pressure not only facilitates removal of the fluid and other materials of the hematoma, but further assists in re-expanding the brain 20 to fill the subdural space 22.

As fluid and other material are evacuated from the subdural space 22 using the pump 46, this fluid/material can be deposited in a discharge reservoir 60. This reservoir 60 can include a sight glass or tube (not shown) through which a user of the system (e.g., physician or physician's assistant) can view the fluid/material that has been evacuated from the subdural space 22. In addition, a relief valve 62 can be associated with the discharge reservoir 60 to enable gas (e.g., air) to exit the reservoir. As is further shown in FIG. 1, an antibacterial filter 64 can be provided between the discharge reservoir 60 and the relief valve 62 to prevent contamination of the closed system during gas discharge.

As can be appreciated from the above discussion, the system 10 is a sterile, closed system in which the subdural hematoma can be replaced with an irrigation fluid and in which the introduction of air into the subdural space can be either completely or nearly eliminated. Preventing the introduction of air into the subdural space is important as it can be associated with post-operative confusion and may predispose the patient to pathological membrane formation and/or recurrence of chronic subdural hematoma.

In some embodiments, the fluid evacuated from the subdural space 22 can be monitored to determine its composition. Among other things, such monitoring can provide an indication as to when the evacuation process can be terminated, i.e., when the fluid being evacuated from the subdural space 22 is primarily irrigation fluid. Accordingly, the system 10 can further include one or monitoring sensors 66. As an example, one such sensor 66 can comprise a spectrophotometer that is configured to measure the spectra of the fluid in the outlet tube 42. Such a measurement can provide the user and the system 10 with an indication of the composition of the fluid, including whether or not it contains gas (e.g., air). Other sensors 66 can be provided to evaluate the fluid for the presence of pathological substances, such as blood, blood breakdown products, proteins, nucleic acid, or ions.

Irrespective of the nature of the data that is collected by the one or more monitoring sensors 66, signals generated by the sensors can be provided to a data acquisition unit 68 that can, for example, amplify and/or modify the signals (e.g., convert the signals from analog to digital signals) before they are provided to a computer system 70, which comprises software and/or firmware that is configured to analyze the signals. Such analysis can include analyzing the spectra measured by the one or more monitoring sensors to provide an indication to a user of the system to end the evacuation procedure. In such a case, flow of irrigation fluid to the subdural space 22 can be halted and the remaining fluid in the subdural space 22 can be evacuated using the pump 46. In other embodiments, the computer system 70 can be configured to automatically shut down the system. It is further noted that software and/or firmware on the computer system 70 can be used to receive pressure data from the pump controller 48 and analyze that data as well. Moreover, the computer system 70 can, in some embodiments, be configured to control operation of the pump controller 48.

Figure 2:
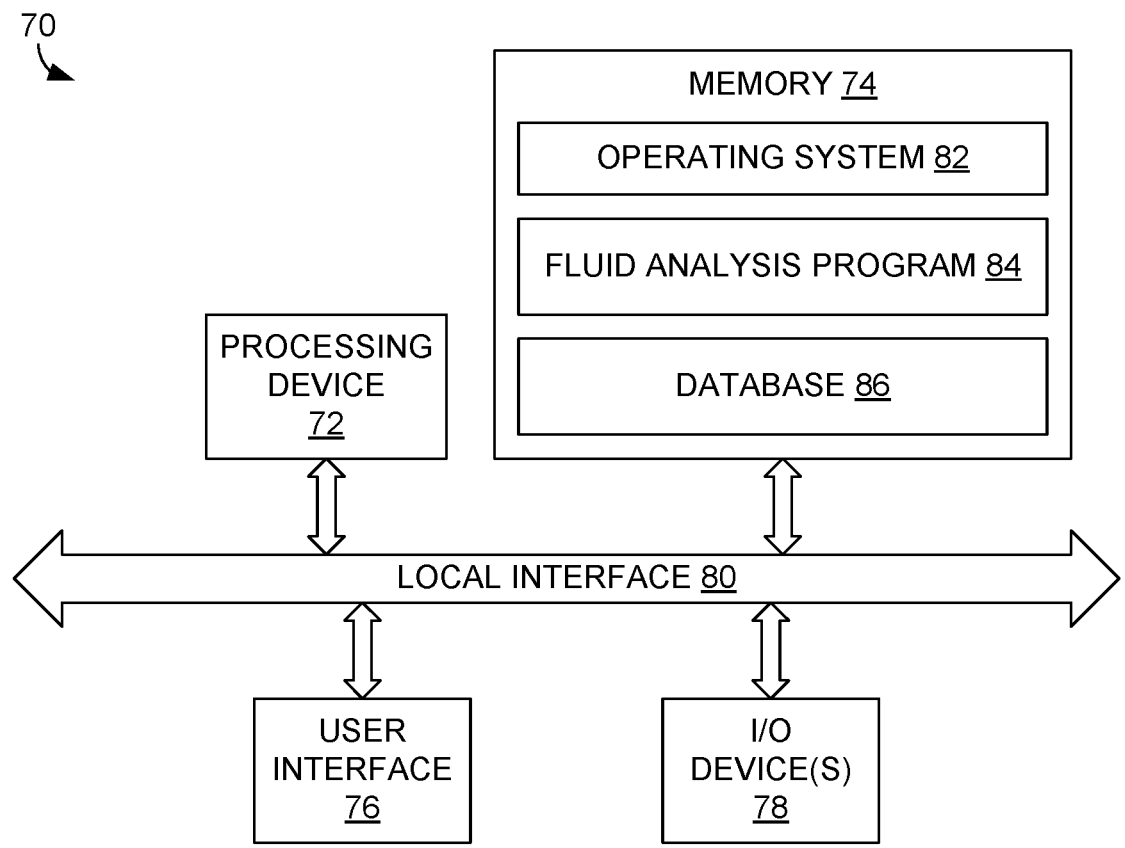
FIG. 2 is a block diagram of an embodiment of a computer system shown in FIG. 1.

FIG. 2 is a block diagram of an example embodiment for the computing system 70. The computing system 70 generally comprises a processing device 72, memory 74, a user interface 76, and one or more input/output (I/O) devices 78, each of which is connected to a system bus 80. The processing device 72 can, for example, include a central processing unit (CPU) that is capable of executing computer-executable instructions stored within the memory 74. The memory 74 can include any one of or a combination of volatile memory elements (e.g., RAM, flash, etc.) and non-volatile memory elements (e.g., hard disk, ROM, etc.). The user interface 76 can comprise one or more devices that can enter user inputs into the computing device 70, such as a keyboard and mouse, as well as one or more devices that can convey information to the user, such as a display. The I/O devices 78 can comprise components that enable the computing device 70 to communicate with other devices, such as a network adapter.

The memory 74 (a non-transitory computer-readable medium) stores software applications (programs) including an operating system 82 and a fluid analysis program 84 that can at least be used to analyze the data received from the monitoring sensor 66 to provide an indication of the composition of the evaluated liquid. As is further shown in FIG. 2, the memory 74 can further include a database 86 in which the results of such analysis can be stored.

The disclosed systems and methods are minimally invasive and may be performed in the operating room or at the bedside. While the current state of the art does not include a quantitative endpoint for evacuation of chronic subdural hematoma, the disclosed systems and methods provide a quantitative measure that enables the clinician to know whether the subdural hematoma has been completely evacuated and an increased time window to achieve complete clearance of pathological substances from the subdural space. This can be paired with routine imaging (e.g., computed tomography) to assess for complete evacuation of subdural hematoma with re-expansion of the brain. In addition, the disclosed systems and methods minimize or eliminate pneumocephalus and tension pneumocephalus and their associated risks and required treatments.

While the current state of the art relies on passive re-expansion of the brain for restoration of the subdural space, the disclosed systems and methods apply negative pressure to the subdural space that may result in more rapid restoration of the subdural space with brain re-expansion, which would lead to improved recovery of neurological deficits caused by brain compression and/or irritation. In addition, it is likely that a more rapid cure of chronic subdural hematoma will decrease the risk of seizures due to brain compression or irritation.

As a further matter, the disclosed systems and methods will likely reduce the risk of early institution of deep venous thrombosis (DVT) chemical prophylaxis (e.g., subcutaneous heparin). Chemical prophylaxis has been shown to be a risk factor for recurrence, and this could be mitigated with continuous drainage of any small amounts of blood products resulting from chemical DVT prophylaxis. This would be expected to lead to decreased risk of DVTs.

Various modifications can be made to the disclosed systems. For example, multiple inlet and/or outlet intracranial bolts can be used for subdural hematomas with mixed densities or that have more than one component separated by one or more membranes (forming discrete hematoma regions), as in the case of a mixed-density subdural hematoma. In addition, the system can further include a tool for opening the dura to enable fluid to be removed.

The invention claimed is:

1. A system for evacuating a subdural hematoma of a patient, the system comprising:
    an external inlet configured to be passed through a first opening formed in a cranium of the patient so as to be placed in fluid communication with a subdural space of the patient;
    an external irrigation reservoir configured to operate outside of the patient, the reservoir being in fluid communication with the external inlet and configured to supply irrigation fluid to the inlet and the subdural space;
    an external outlet separate from the external inlet configured to be passed through a second opening formed in the cranium so as to also be placed in fluid communication with the subdural space; and
    an external pump configured to operate outside of the patient, the pump being in fluid communication with the external outlet and configured to create negative pressure within the subdural space and evacuate fluid from the subdural space.

2. The system of claim 1, wherein the external inlet comprises a first intracranial bolt and the external outlet comprises a second intracranial bolt, each intracranial bolt including an internal passage through which the fluid can pass.

3. The system of claim 2, wherein the external inlet further comprises an inlet manifold connected to the first intracranial bolt and the external outlet further comprises an outlet manifold connected to the second intracranial bolt.

4. The system of claim 1, wherein the pump comprises a peristaltic pump.

5. The system of claim 1, further comprising at least one pressure sensor configured to measure pressure within the external inlet, the external outlet, or the subdural space.

6. The system of claim 5, wherein the at least one pressure sensor comprises a first pressure sensor associated with the external inlet and a second pressure sensor associated with the external outlet.

7. The system of claim 6, wherein the first pressure sensor is integrated into the external inlet and the second pressure sensor is integrated into the external outlet.

8. The system of claim 5, further comprising a pump controller in communication with the at least one pressure sensor and configured to control operation of the external pump responsive to the measured pressure.

9. The system of claim 5, further comprising a discharge reservoir in which fluid evacuated from the subdural space by the external pump is collected.

10. The system of claim 1, further comprising a monitoring sensor in fluid communication with the external outlet configured to collect data relevant to a parameter of the fluid evacuated from the subdural space.

11. The system of claim 10, wherein the monitoring sensor is configured to collect data relevant to one or more of spectra of the evacuated fluid, the composition of the evacuated fluid, or the presence of pathological substances in the evacuated fluid.

12. The system of claim 11, further comprising a computing system configured to analyze the data collected by the monitoring sensor.

13. The system of claim 1, wherein the system comprises multiple external inlets and multiple external outlets configured to be placed in fluid communication with the subdural space.

14. A method for evacuating a subdural hematoma, the method comprising:
    forming an inlet opening in the cranium of the patient to access the subdural space in which the subdural hematoma lies;
    forming an outlet opening in the cranium spaced from the inlet opening to access the subdural space;
    supplying an irrigation fluid to the subdural space through the inlet opening; and
    simultaneously applying negative pressure to the subdural space with a pump associated with the outlet opening and evacuating fluid from the subdural space.

15. The method of claim 14, further comprising measuring pressure within the subdural space and controlling the negative pressure in response to the measured pressure.

16. The method of claim 15, wherein applying negative pressure comprises maintaining the subdural space at a pressure of approximately −1 to −8 mmHg.

17. The method of claim 14, further comprising monitoring the fluid evacuated from the subdural space via the outlet.

18. The method of claim 17, wherein monitoring the fluid comprises monitoring the fluid to collect data relevant to one or more of spectra of the evacuated fluid, the composition of the evacuated fluid, or the presence of pathological substances in the evacuated fluid.

19. The method of claim 18, further comprising analyzing the collected data using a computing device.

20. The method of claim 14, comprising forming multiple inlet openings and multiple outlet openings in the cranium so as to access different regions of a mixed-density subdural hematoma.

21. A system comprising:
    an external inlet configured to be passed through a first opening formed in a cranium of a patient so as to be placed in fluid communication with a subdural space of the patient;
    an external outlet separate from the external inlet configured to be passed through a second opening formed in the cranium so as to also be placed in fluid communication with the subdural space, wherein fluid within the subdural space can exit the space through the outlet; and
    a monitoring sensor configured collect data relevant to the presence of one or more pathological substances within the fluid that exits the subdural space.

22. The system of claim 21, wherein the monitoring sensor is configured to collect data relevant to the presence of one or more of blood, blood breakdown products, proteins, nucleic acid, or ions within the fluid.

23. The system of claim 21, wherein the monitoring sensor comprises a spectrophotometer configured to measure the spectra of the fluid.

24. The system of claim 21, further comprising a computing system configured to analyze the data collected by the monitoring sensor.

25. A method comprising:

forming an inlet opening in a cranium of a patient to access a subdural space of the patient in which a subdural hematoma lies;

delivering irrigation fluid through the inlet opening and into the subdural space;

forming an outlet opening in the cranium spaced from the inlet opening to access the subdural space, wherein fluid within the subdural space can exit the space via the outlet; and monitoring the fluid that exits the subdural space to collect data relevant to the presence of one or more pathological substances within the fluid.

26. The method of claim 25, wherein collecting data relevant to the presence of one or more pathological substances comprises collecting data relevant to the presence of one or more of blood, blood breakdown products, proteins, nucleic acid, or ions within the fluid.

27. The method of claim 25, wherein monitoring the fluid comprises monitoring the fluid using a spectrophotometer configured to measure the spectra of the fluid.

28. The method of claim 25, further comprising analyzing the collected data using a computing system.

* * * * *